United States Patent
Balaganesan et al.

(10) Patent No.: US 9,812,654 B2
(45) Date of Patent: Nov. 7, 2017

(54) PHOSPHORESCENT MATERIALS FOR ORGANIC ELECTROLUMINESCENT DEVICES

(71) Applicant: E-RAY OPTOELECTRONICS TECHNOLOGY CO., LTD., Chung-Li, Taiwan (TW)

(72) Inventors: Banumathy Balaganesan, Chung-Li (TW); Heh-Lung Huang, Chung-Li (TW); Huang-Ming Guo, Chung-Li (TW); Po-Wei Hsu, Chung-Li (TW)

(73) Assignee: E-RAY OPTOELECTRONICS TECHNOLOGY CO., LTD., Chung-Li (TW)

( * ) Notice: Subject to any disclaimer, the term of this patent is extended or adjusted under 35 U.S.C. 154(b) by 176 days.

(21) Appl. No.: 14/741,686

(22) Filed: Jun. 17, 2015

(65) Prior Publication Data
US 2015/0372242 A1    Dec. 24, 2015

Related U.S. Application Data

(60) Provisional application No. 62/013,626, filed on Jun. 18, 2014.

(51) Int. Cl.
*H01L 51/50*    (2006.01)
*H01L 51/00*    (2006.01)
(Continued)

(52) U.S. Cl.
CPC ........ *H01L 51/0074* (2013.01); *C07D 471/04* (2013.01); *C07D 487/04* (2013.01);
(Continued)

(58) Field of Classification Search
None
See application file for complete search history.

(56) References Cited

FOREIGN PATENT DOCUMENTS

JP    WO 2013137001 A1 *   9/2013    ............. H01L 51/50

* cited by examiner

*Primary Examiner* — Gregory Clark
(74) *Attorney, Agent, or Firm* — Amin, Turocy & Watson LLP

(57) ABSTRACT

The present invention provides a high triplet energy compound of Formula 1 for an organic electroluminescent device:

Formula 1

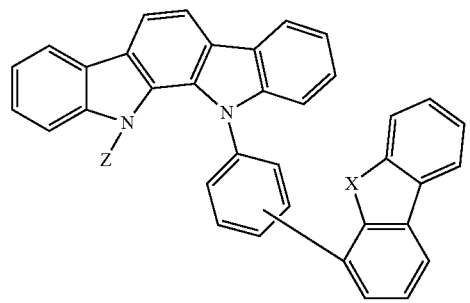

In Formula 1, X represents an oxygen or a sulfur atom, and represents a substituted or unsubstituted hetero-aromatic ring containing at least two nitrogens or an alkyl group with C2 to C6. The organic electroluminescent device including the compound used in an emissive layer or an electron transporting layer enhances the efficiency and the stability of the device.

5 Claims, 5 Drawing Sheets

(51) Int. Cl.
*C07D 487/04* (2006.01)
*C09K 11/06* (2006.01)
*C07D 471/04* (2006.01)

(52) U.S. Cl.
CPC .......... *C09K 11/06* (2013.01); *H01L 51/0067* (2013.01); *H01L 51/0072* (2013.01); *H01L 51/0073* (2013.01); *C09K 2211/1007* (2013.01); *C09K 2211/1044* (2013.01); *C09K 2211/1059* (2013.01); *C09K 2211/1088* (2013.01); *C09K 2211/1092* (2013.01); *C09K 2211/185* (2013.01); *H01L 51/0085* (2013.01); *H01L 51/5016* (2013.01); *H01L 2251/5384* (2013.01)

PHOSPHORESCENT MATERIALS FOR ORGANIC ELECTROLUMINESCENT DEVICES

BACKGROUND OF THE INVENTION

1. Field of the Invention

The present invention relates to a non-emissive material of Formula 1 and a composition including the same for fabricating an organic electroluminescent device.

2. Description of Related Art

Organic light-emitting devices (OLEDs) are gaining attraction in the recent years as the active displays owing to their characteristics such as high brightness, quick refresh rate and wide color gamut and are more suitable for portable electronic applications.

In general, an OLED includes an anode, a hole transport layer, an emitting layer, an electron transport layer and a cathode, which are deposited one over the other sequentially, by means of vacuum deposition or coating techniques. When a voltage is applied, the anode injects holes and the cathode injects electrons into the organic layer(s). The injected holes migrate to the emitting layer through the hole transporting layer and the electrons migrate to the light emitting layer through the electron transporting layer. In the emitting layer, the holes and electrons recombine to produce excitons. Light is emitted when the exciton relaxes through a photoemissive mechanism.

The reason for manufacturing an organic electroluminescent (EL) display with a multi-layered thin film structure includes stabilization of the interfaces between the electrodes and the organic layers. In addition, in organic materials, the mobility of electrons and holes significantly differ, and thus, if appropriate hole transporting and electron transporting layers are used, holes and electrons can be efficiently transferred to the luminescent layer. Also, if the density of the holes and electrons are balanced in the emitting layer, luminous efficiency can be increased. The proper combination of organic layers described above can enhance the device efficiency and lifetime. However, it has been very difficult to find an organic material that satisfies all the requirements for use in practical display applications.

The initial OLEDs used emissive materials that emitted light from their singlet states, termed as "fluorescence". Fluorescent emission generally occurs in a time frame of less than 10 nanoseconds. Several OLED materials and device configurations utilizing fluorescence are described in U.S. Pat. No. 4,769,292, U.S. Pat. No. 5,844,363, and U.S. Pat. No. 5,707,745, which are incorporated herein by reference in their entirety.

More recently, OLEDs having emissive materials that emit light from triplet states ("phosphorescence") have been demonstrated in literature, Nature, 1998, No. 395, p. 151 and Appl. Phys. Lett., 1999, No. 3, p. 4, and patent document U.S. Pat. No. 7,279,704, which are incorporated herein by reference in their entirety.

For a high luminous and efficient phosphorescent OLED's, a host material must have non-emissive high triplet energy and a balanced electrical charge (hole/electron) injection/transport characteristics. Moreover, the host material should also possess good electrochemical stability, high thermal resistance and excellent thin film stability. However, compound capable of satisfying all the said properties from practical considerations have not been known till date.

Patent documents such as WO2003-78451, WO2005-76668, US2006-51616, JP2008-280330, WO2008-123189, JP 2009-21336 Attempts have shown materials having excellent bipolar transport characteristics; however, due to mismatch of the energy levels of the molecular orbitals with the adjacent layers in the organic electroluminescent devices, the challenges still remain in achieving high efficiency and good device stability.

SUMMARY OF THE INVENTION

The present invention has been made in order to solve the problems described above, and an object thereof is to provide an organic compound, which is used as an phosphorescent host material in an emitting layer or as ab electron transport material, or an exciton blocking layer in an organic light emitting device, and thereby improving the device luminance efficiency and the stability. More particularly, the present invention describes various compounds with a triplet energy more than 2.5 eV, having superior electron transport properties resulting in efficient and stable organic EL devices.

The present invention provides an organic material having the following Formula (I)

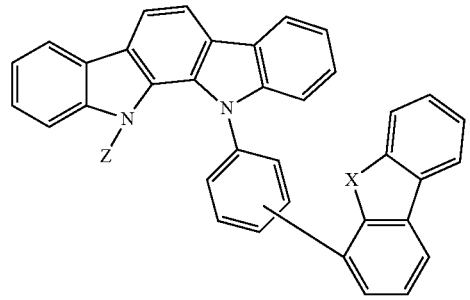

Formula 1 wherein X represents an oxygen or a sulfur atom; Z represents a substituted or unsubstituted hetero-aromatic ring containing at least two nitrogens or an alkyl group with C2 to C6.

In an aspect of the present invention, the triplet energy of the materials represented by the formula 1, more than 2.5 eV.

In another aspect of the present invention, a process for producing the specific compounds represented by the Formula 1 is provided.

In a further aspect of the present invention, an organic electroluminescent device that utilizes the aforementioned compound in the organic layer, whose thickness is more than 1 nm but less than 500 nm, is provided.

The compound represented by the Formula 1 according to the present invention is capable of being made into an amorphous thin film by means of vacuum deposition or wet process, for organic electroluminescent devices.

DETAILED DESCRIPTION OF THE PREFERRED EMBODIMENTS

Figure 1:
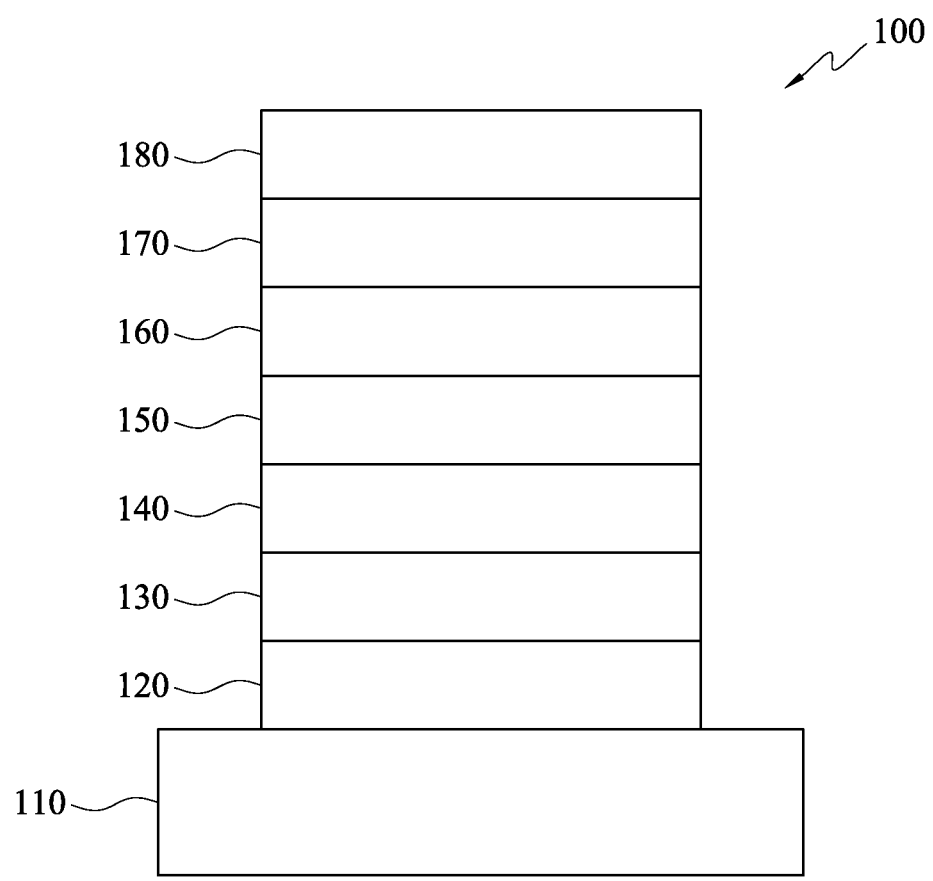
FIG. 1 is a cross-sectional view illustrating one example of an organic light emitting according to an embodiment of the present invention.

The detailed description of the present invention is illustrated by the following specific examples. Persons skilled in the art can conceive the other advantages and effects of the present invention based on the disclosure contained in the specification of the present invention.

A compound for an organic electroluminescent device according to this invention is represented by the Formula 1.

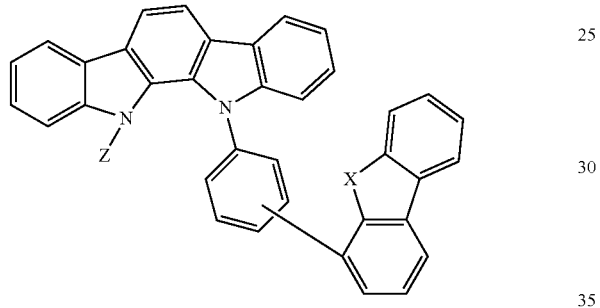

Formula 1

In Formula 1, X represents an oxygen or a sulfur atom; Z represents a substituted or unsubstituted hetero-aromatic ring containing at least two nitrogens or an alkyl group with C2 to C6; Preferable examples of the compounds represented by the aforementioned Formula 1 are shown in Table 1, but not limited thereto.

TABLE 1

| Compound | Structure |
|---|---|
| F1 | |
| F2 | 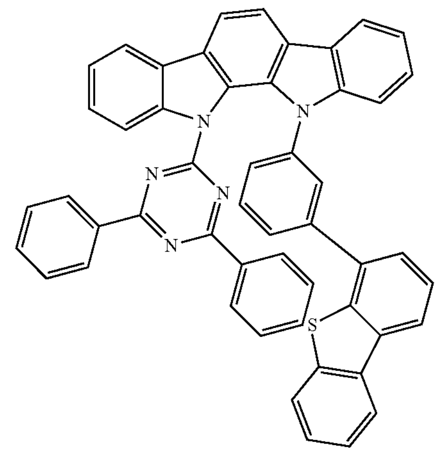 [SMILES: c1ccc(-c2nc(-c3ccccc3)nc(-n3c4ccccc4c4ccc5c6ccccc6n(-c6cccc(-c7cccc8c7sc7ccccc78)c6)c5c43)n2)cc1] |
| F3 | 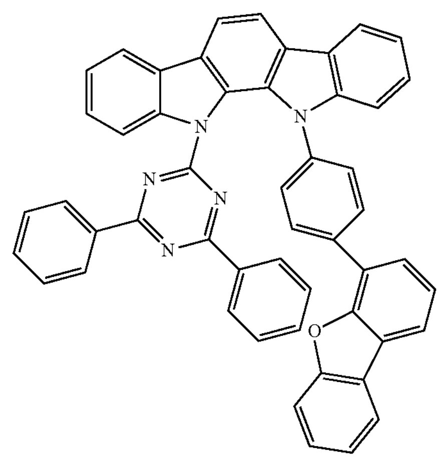 [SMILES: c1ccc(-c2nc(-c3ccccc3)nc(-n3c4ccccc4c4ccc5c6ccccc6n(-c6ccc(-c7cccc8c7oc7ccccc78)cc6)c5c43)n2)cc1] |
| F4 | 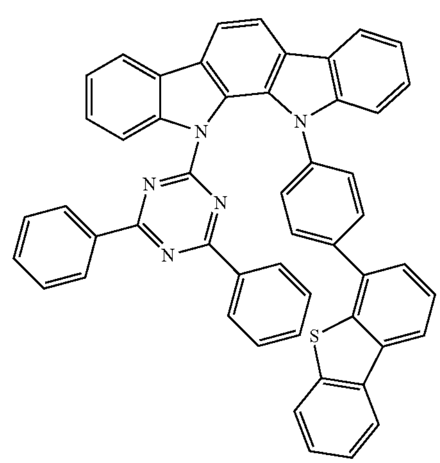 |

TABLE 1-continued
| Compound | Structure |
|---|---|
| F5 | 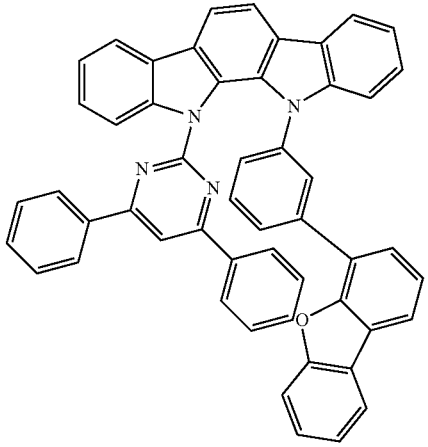 [SMILES: c1ccc(-c2cc(-c3ccccc3)nc(-n3c4ccccc4c4ccc5c6ccccc6n(-c6cccc(-c7cccc8c7oc7ccccc78)c6)c5c43)n2)cc1] |
| F6 | 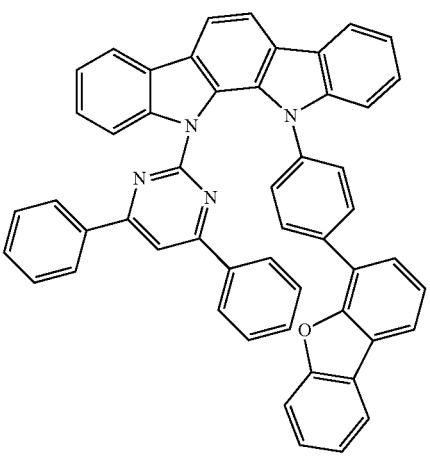 |
| F7 | 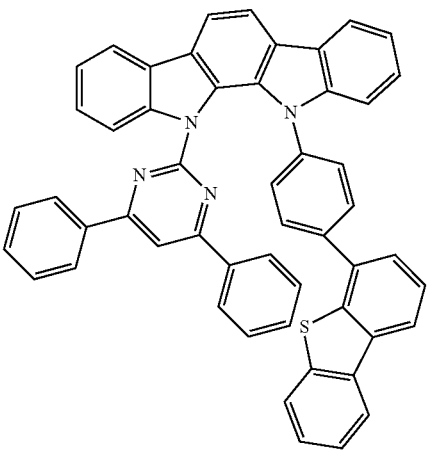 [SMILES: c1ccc(-c2cc(-c3ccccc3)nc(-n3c4ccccc4c4ccc5c6ccccc6n(-c6ccc(-c7cccc8c7oc7ccccc78)cc6)c5c43)n2)cc1] |
| F8 | 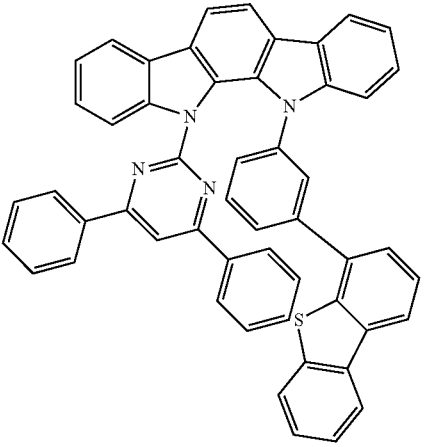 [SMILES: c1ccc(-c2cc(-c3ccccc3)nc(-n3c4ccccc4c4ccc5c6ccccc6n(-c6cccc(-c7cccc8c7sc7ccccc78)c6)c5c43)n2)cc1] |
| F9 | 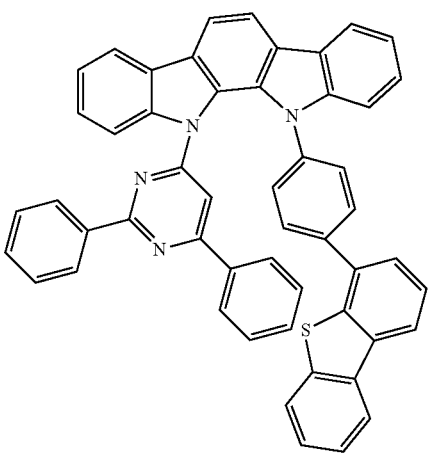 [SMILES: c1ccc(-c2cc(-n3c4ccccc4c4ccc5c6ccccc6n(-c6ccc(-c7cccc8c7sc7ccccc78)cc6)c5c43)nc(-c3ccccc3)n2)cc1] |
| F10 | 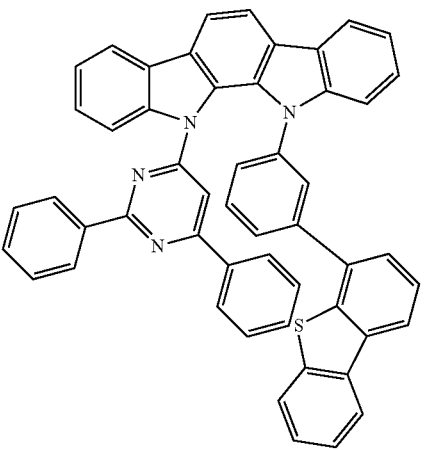 [SMILES: c1ccc(-c2cc(-n3c4ccccc4c4ccc5c6ccccc6n(-c6cccc(-c7cccc8c7sc7ccccc78)c6)c5c43)nc(-c3ccccc3)n2)cc1] |

TABLE 1-continued
| Compound | Structure |
|---|---|
| F11 | 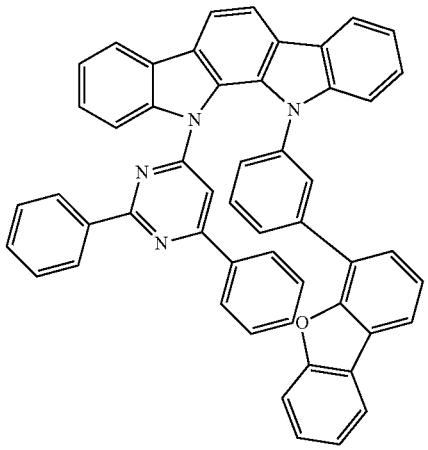 [SMILES: c1ccc(-c2cc(-n3c4ccccc4c4ccc5c6ccccc6n(-c6cccc(-c7cccc8c7oc7ccccc78)c6)c5c43)nc(-c3ccccc3)n2)cc1] |
| F12 | 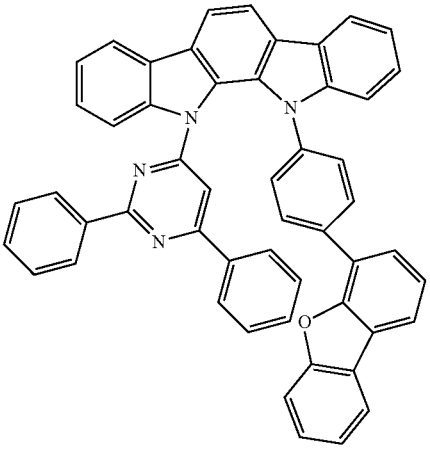 [SMILES: c1ccc(-c2cc(-n3c4ccccc4c4ccc5c6ccccc6n(-c6ccc(-c7cccc8c7oc7ccccc78)cc6)c5c43)nc(-c3ccccc3)n2)cc1] |
| F13 | 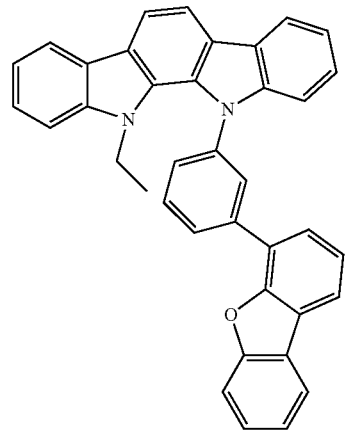 [SMILES: CCn1c2ccccc2c2ccc3c4ccccc4n(-c4cccc(-c5cccc6c5oc5ccccc56)c4)c3c21] |
| F14 | 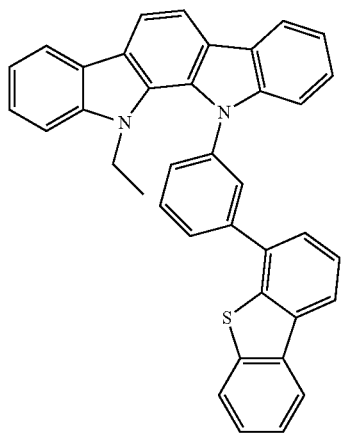 [SMILES: CCn1c2ccccc2c2ccc3c4ccccc4n(-c4cccc(-c5cccc6c5sc5ccccc56)c4)c3c21] |
| F15 | 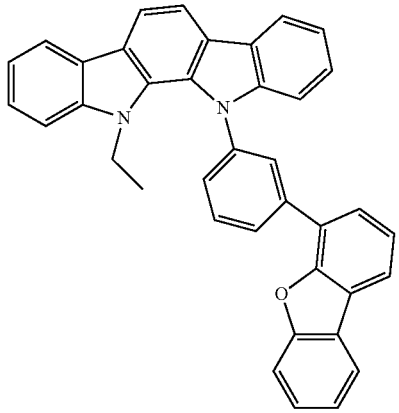 [SMILES: CCn1c2ccccc2c2ccc3c4ccccc4n(-c4cccc(-c5cccc6c5oc5ccccc56)c4)c3c21] |
| F16 | 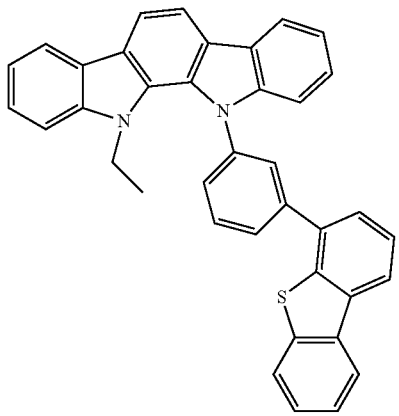 [SMILES: CCn1c2ccccc2c2ccc3c4ccccc4n(-c4cccc(-c5cccc6c5sc5ccccc56)c4)c3c21] |

TABLE 1-continued
| Compound | Structure |
|---|---|
| F17 | 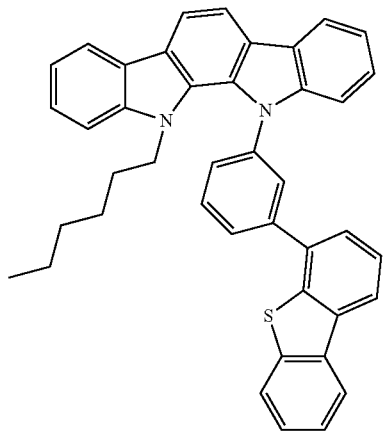 [SMILES: CCCCCCn1c2ccccc2c2ccc3c4ccccc4n(-c4cccc(-c5cccc6c5sc5ccccc56)c4)c3c21] |
| F18 | 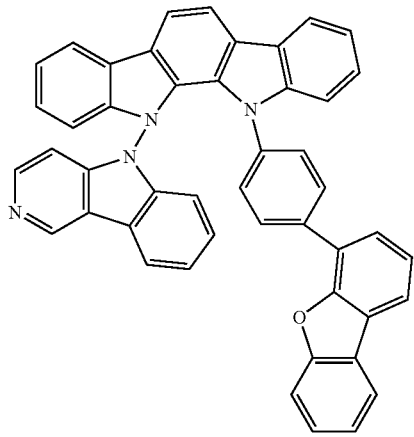 [SMILES: c1ccc2c(c1)oc1c(-c3ccc(-n4c5ccccc5c5ccc6c7ccccc7n(-n7c8ccccc8c8cnccc87)c6c54)cc3)cccc12] |
| F19 | 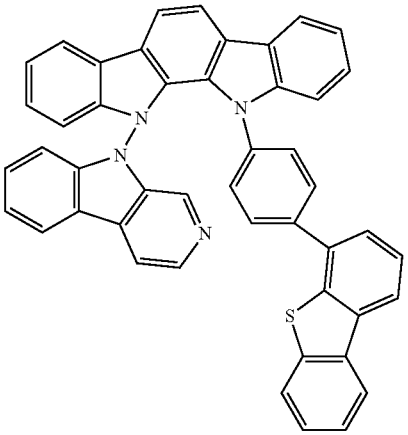 [SMILES: c1ccc2c(c1)sc1c(-c3ccc(-n4c5ccccc5c5ccc6c7ccccc7n(-n7c8ccccc8c8ccncc87)c6c54)cc3)cccc12] |
| F20 | 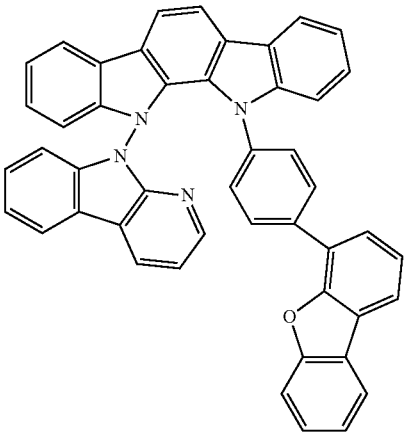 [SMILES: c1ccc2c(c1)oc1c(-c3ccc(-n4c5ccccc5c5ccc6c7ccccc7n(-n7c8ccccc8c8cccnc87)c6c54)cc3)cccc12] |
Exemplary compounds F1 to F20, represented by formula 1, may be prepared by, but not limited to, a sequence of reactions as shown in the synthetic schemes 1-4.

Synthetic Scheme 1:
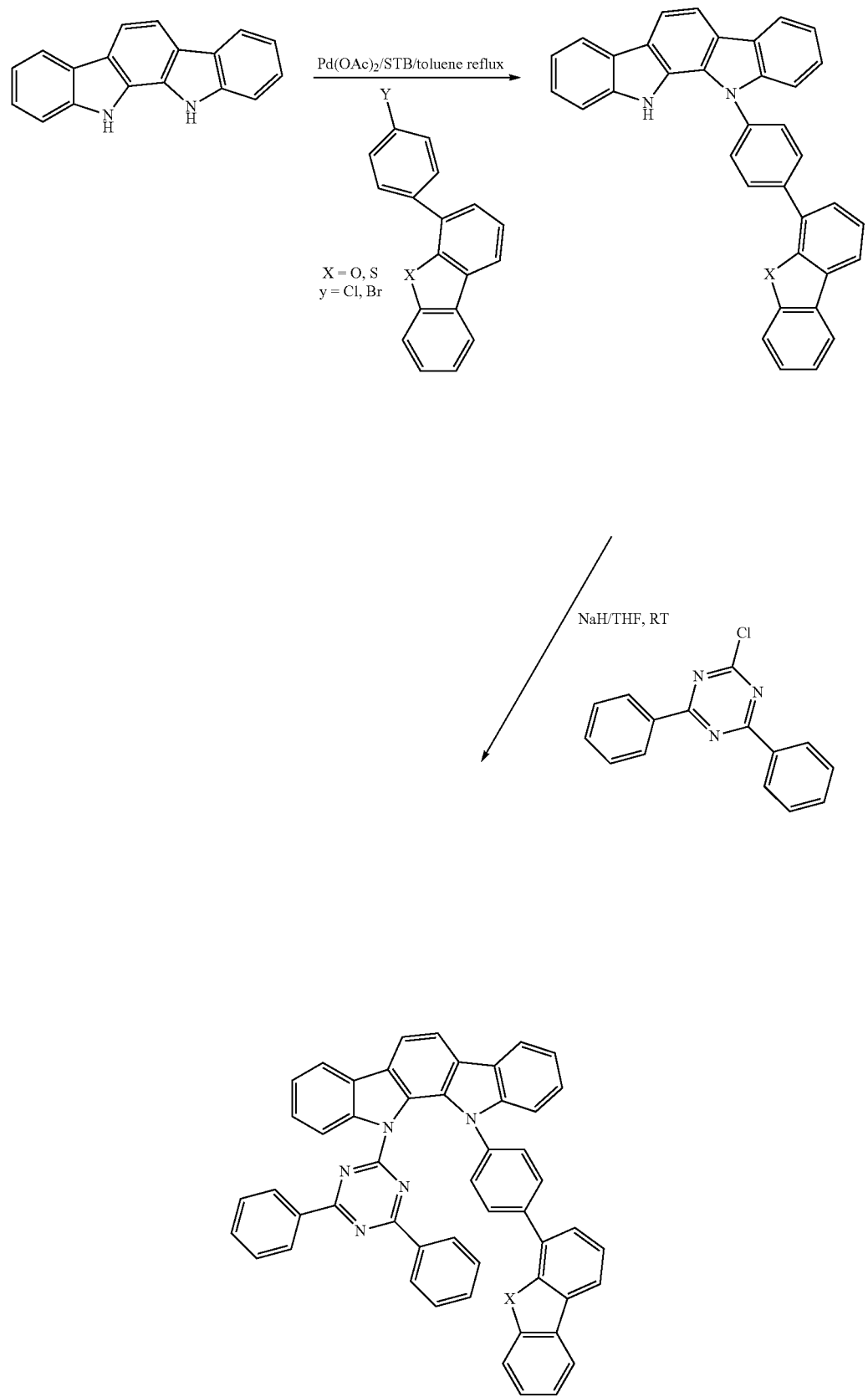

Synthetic Scheme 2:
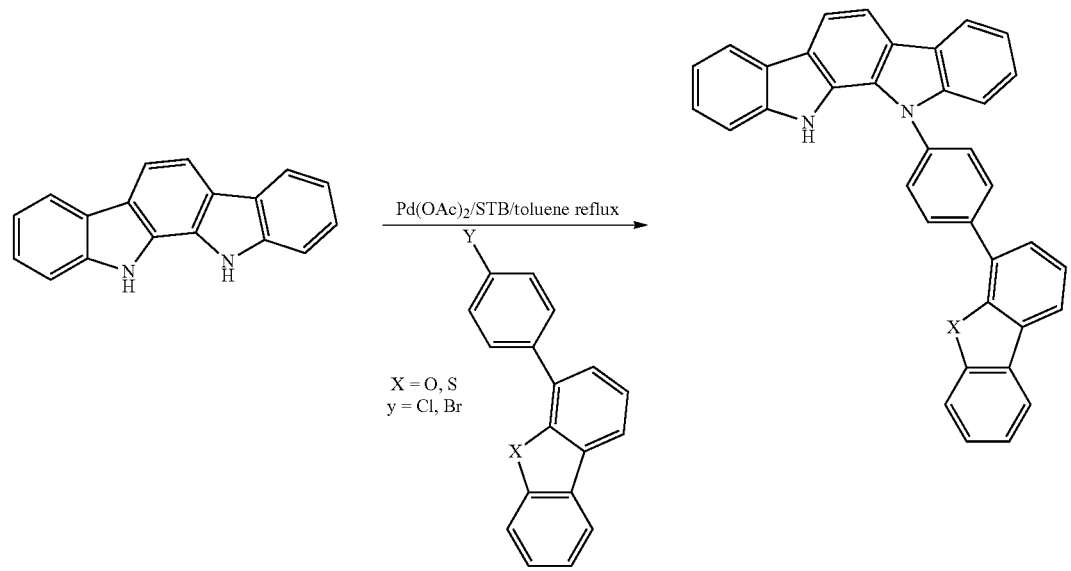
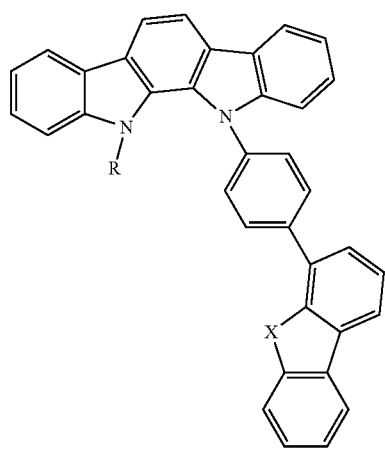

Synthetic Scheme 3:
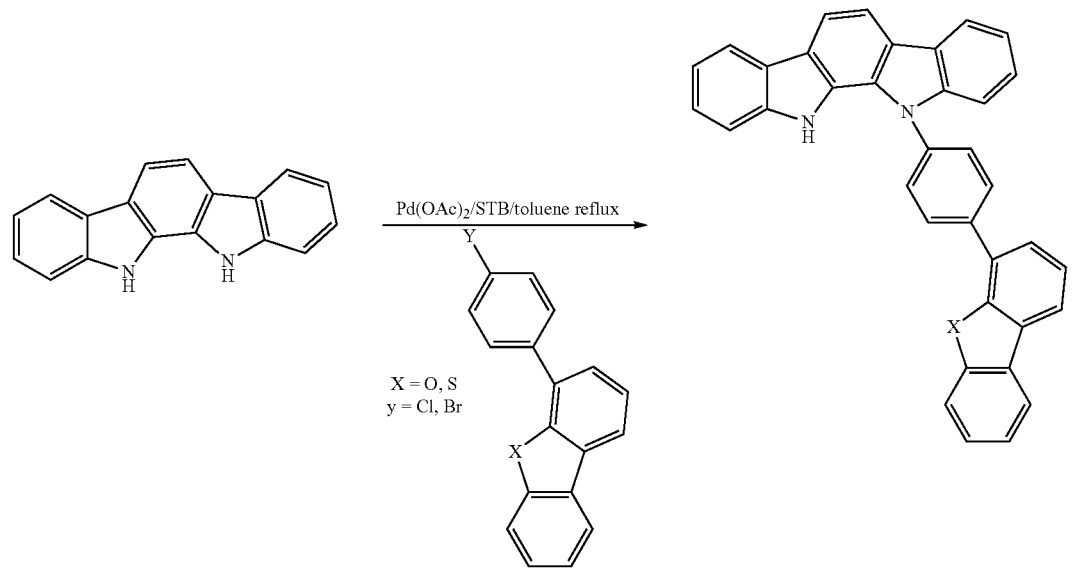
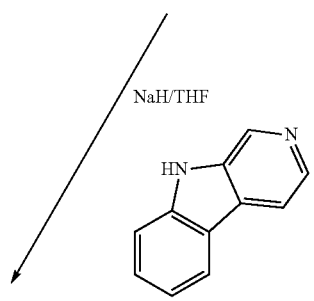
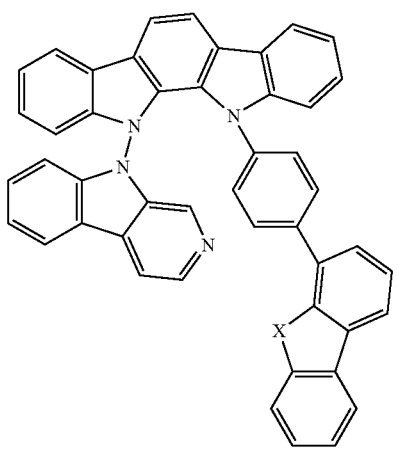

Synthetic Scheme 4:

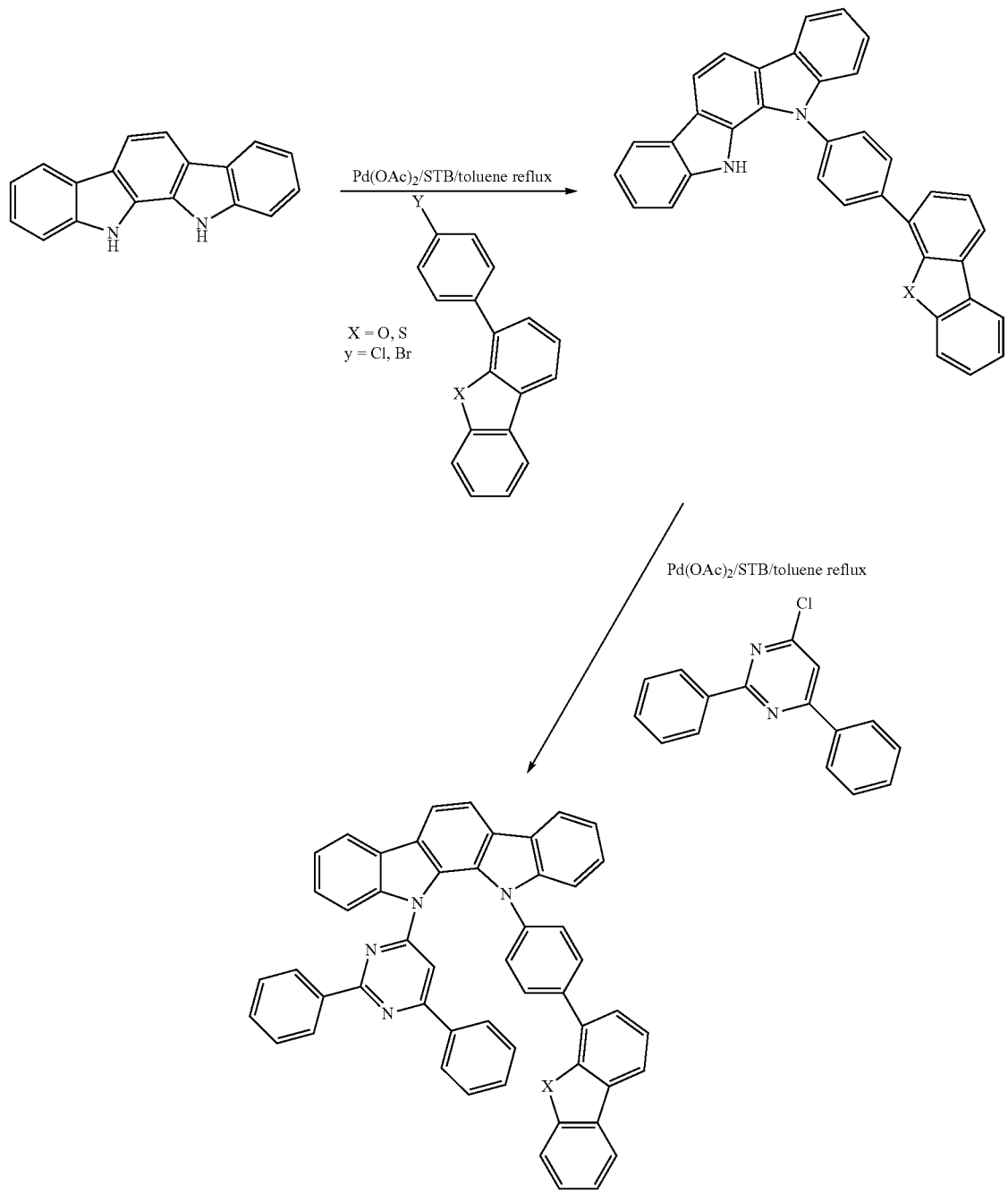

The organic electroluminescent device of this invention has at least one light emitting layer disposed between an anode and a cathode piled one upon another on a substrate, and the light emitting layer includes a phosphorescent dopant and the aforementioned compound represented by formula 1, as a host material. It is preferable that a hole injecting/transporting layer is disposed between the anode and the light emitting layer, and an electron injecting/transporting layer is disposed between the cathode and the light emitting layer. It is also preferable that either a hole blocking layer is disposed between the light emitting layer and the electron injecting/transporting layer, or an electron blocking layer is disposed between the hole injecting/transporting layer and the light emitting layer.

Further, the compounds represented by any of formula 1 may be used in the electron injecting/transporting layer or hole blocking layer and/or electron blocking layer.

Phosphorescent dopants to be used in the light emitting layer are preferably organic metal complexes containing at least one metal selected from ruthenium, rhodium, palladium, silver, rhenium, osmium, iridium, platinum, and gold. Such organic metal complexes are known in the aforementioned patent documents and elsewhere and a suitable complex can be selected from them and used in this invention.

Preferable phosphorescent dopants include complexes having a noble metal element such as Ir in the center, typically Ir(ppy)$_3$, complexes such as Ir(bt)$_2$(acac), FIrpic, and complexes such as PtOEt$_3$, but are not limited thereto.

The content of the aforementioned phosphorescent dopant in the light emitting layer is preferably in the range of 3 wt % to 10 wt %.

Preferred Embodiments of the Present Invention

The structure of the organic EL device of this invention will be explained with reference to the drawing, but not limited thereto.

FIG. 1, which illustrates an embodiment, is a schematic showing an organic light emitting device 100. Device 100 may include a substrate 110, an anode 120, a hole injection layer 130, a hole transporting layer 140, an emissive layer 150, an electron transporting layer 160, an electron injection layer 170, and a cathode 180. Device 100 may be fabricated by depositing the layers described, in order.

Figure 2:
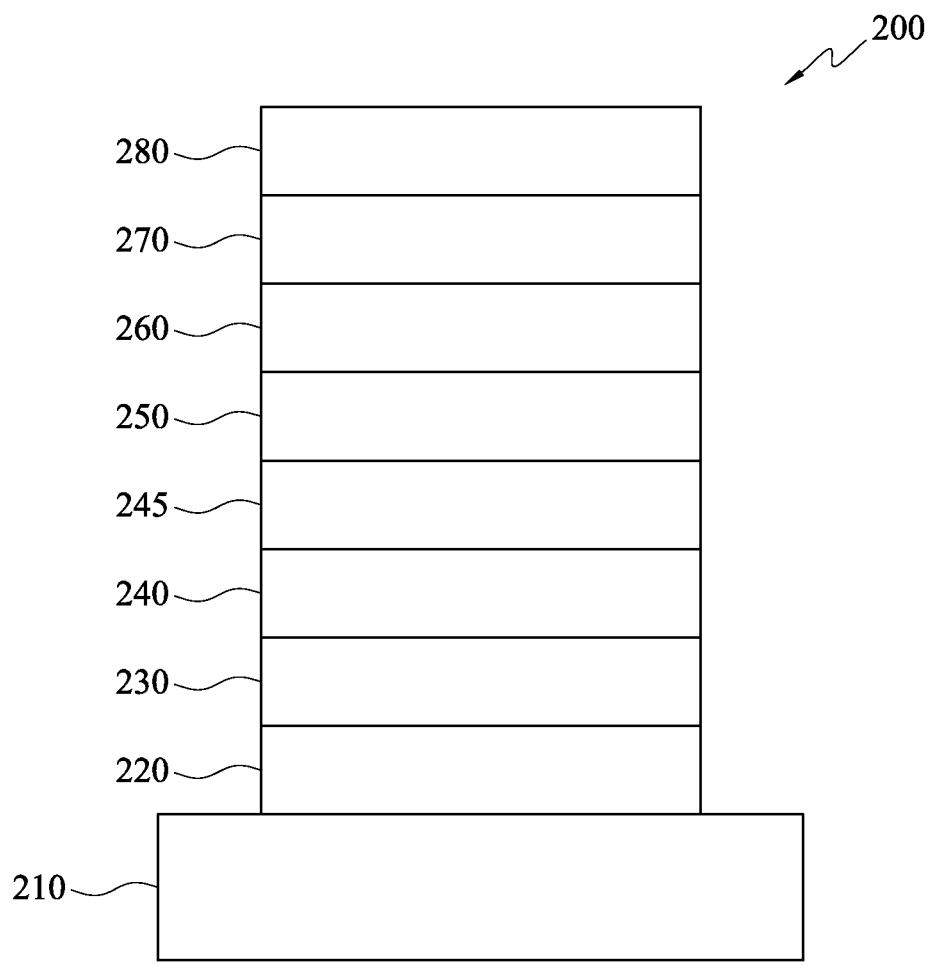
FIG. 2 is a cross-sectional view illustrating another example of an organic light emitting device according to another embodiment of the present invention.
Figure 3:
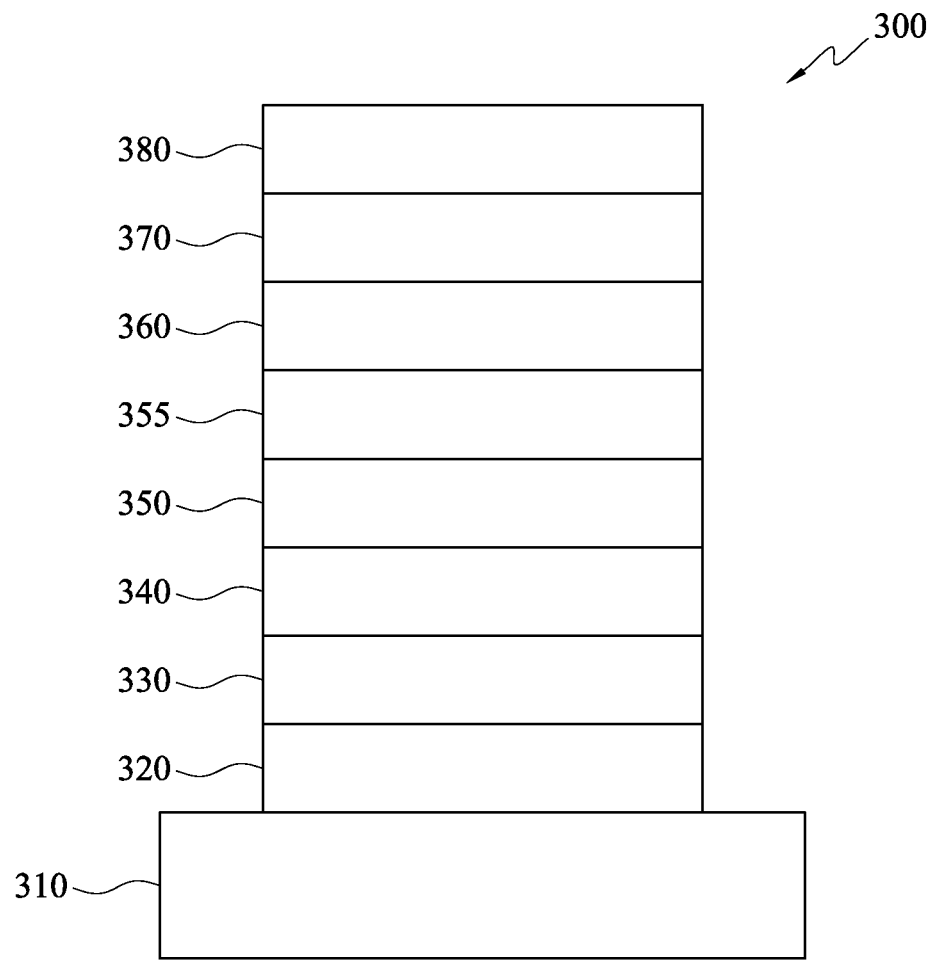
FIG. 3 is a cross-sectional view illustrating yet another example of an organic light emitting device according to another embodiment of the present invention.

FIG. 2, which illustrates an embodiment, is a schematic showing an organic light emitting device 200. Device 200 may include a substrate 210, an anode 220, a hole injection layer. 230, a hole transporting layer 240, an excition blocking layer 245, an emissive layer 250, an electron transporting layer 260, an electron injection layer 270, and a cathode 280;

FIG. 3, which illustrates an embodiment, is a schematic showing an organic light emitting device 300. Device 300 may include a substrate 310, an anode 320, a hole injection layer 330, a hole transporting layer 340, an emissive layer 350, an exciton blocking layer 355, an electron transporting layer 360, an electron injection layer 370, and a cathode 380;

It is possible to fabricate a device with a structure that is the reverse of the one shown in FIGS. 1-3. In this case of the reverse structure, a layer or layers may be added or omitted as needed.

Materials used in a hole injection layer, a hole transporting layer, an electron blocking layer, a hole blocking layer, an electron transporting layer, or an electron injection layer, may be selected from those reported in the literature cited elsewhere.

Organic EL device of this invention is applicable to a single device, a device with its structure arranged in array, or a device in which the anode and the cathode are arranged in X-Y matrix. The organic EL device of this invention produces significant improvement in lifetime stability over the conventional devices for phosphorescent OLED device structures.

Materials used in a hole injection layer, a hole transport layer, an electron blocking layer, a hole blocking layer, an electron transport layer, or an electron injection layer may be selected from those reported in the literature cited elsewhere.

For example, an electron-transporting material forming the electron-transporting layer differs from the material forming the light emitting layer and has hole-transporting properties, so as to facilitate the hole mobility in the electron-transporting layer, and to prevent accumulation due to the difference in ionization potential between the light emitting layer and the electron-transporting layer can be prevented.

In addition, U.S. Pat. No. 5,844,363, which is incorporated by reference in its entirety, discloses a flexible and transparent substrate-anode combination. An example of a p-doped hole transport layer is m-MTDATA doped with F$_4$-TCNQ at a molar ratio of 50:1, as disclosed in US Patent Application Publication No. 20030230980, which is incorporated by reference in its entirety. An example of an n-doped electron transport layer is BPhen doped with Li at a molar ratio of 1:1, as disclosed in US Patent Application Publication No. 20030230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in U.S. Pat. No. 6,097,147 and US Patent Application Publication No. 20030230980, which are incorporated by reference in their entireties. Examples of injection layers are provided in US Patent Application Publication No. 20040174116, which is incorporated by reference in its entirety. A description of protective layers may be found in US Patent Application Publication No. 20040174116, which is incorporated by reference in its entirety.

Structures and materials not specifically described may also be used, such as OLEDs comprised of polymeric materials (PLEDs) such as disclosed in U.S. Pat. No. 5,247,190, which is incorporated by reference in its entirety. Further, OLEDs having a single organic layer may be used. OLEDs may be stacked as described in U.S. Pat. No. 5,707,745, which is incorporated by reference in its entirety.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102, which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with deposition methods such as ink-jet and OVJD. Certainly, other methods may be used. The materials to be deposited may be modified to make them compatible with a particular deposition method.

An organic electroluminescent device of this invention is applicable to a single device, a device with its structure arranged in array, or a device having the anode and the cathode arranged in an X-Y matrix. The present invention significantly improves luminous efficiency and driving stability of an organic electroluminescent device over the conventional devices, when used in combination of phosphorescent dopants in the light emitting layer, and furthermore the organic electroluminescent device of the present invention can perform better when applied to full-color or multicolor panels.

EXAMPLES

This invention will be described in more detail below with reference to the examples; however, it will not be limited to these examples and it can be reduced to practice in various modes unless such practice exceeds the substance of this invention.

All of the intermediates used in the synthesis examples disclosed in this patent are prepared following the methods cited elsewhere.

Synthesis Example 1 (Synthesis of Compound F1)

In a 2 L flask, a mixture of 4-(3-chlorophenyl) dibenzo[b,d]furan (38.0 g), 11,12-dihydroindolo[2,3-a]carbazole (35 g), bis(dibenzylideneacetone)palladium(0) (2.3 g), sodium-tert-butoxide (39.3 g), xylene (875 ml), tri-tert-butylphosphine (2.21) were added, and refluxed under nitrogen atmosphere. The reaction was monitored by thin layer chromatography. After the completion of the reaction, the reaction mixture was quenched with water (500 ml), and extracted using ethyl acetate (500 ml). The organic layer was extracted with water (5×250 ml), and dried over anhydrous sodium sulfate. The collected ethyl acetate layer passed through celite column chromatography for further purification; Subsequently, the ethyl acetate layer was evaporated to dryness in a rotary evaporator under vacuum. The residue was further precipitated by adding 500 ml n-hexane, filtered and dried under vacuum to yield 11-(3-(dibenzo[b,d]furan-4-yl)phenyl)-11,12-dihydroindolo[2,3-a]-carbazole. in 51 g.

In a 1 L flask, a mixture of 11-(3-(dibenzo[b,d]furan-4-yl)phenyl)-11,12-dihydroindolo carbazole (50 g), sodium hydride (69.4 g), tetrahydrofuran (500 ml) was added, and stirred at 40° C. under nitrogen atmosphere. After an hour, 2-chloro-4,6-diphenyl-1,3,5-triazine (32 g) was added and continued stirring overnight. The reaction was monitored by thin layer chromatography. After the completion of the reaction, the reaction mixture was quenched with water (200 ml) and extracted using ethyl acetate (300 ml). The organic layer was extracted with water (3×150 ml), and dried over anhydrous sodium sulfate. The collected ethyl acetate layer passed through celite column chromatography for further purification. Subsequently, the ethyl acetate layer was evaporated to dryness in a rotary evaporator under vacuum. The residue was further precipitated by adding 300 ml methanol, filtered and dried under vacuum. Compound F1 was obtained as a light yellow colored solid in 36.1 g (49% yield) with a hplc purity of 99%.

Compound F1 showed a melting point of 251° o and a glass transition temperature of 144° a.

1H NMR (CDCl3, 400 MHz) δ: 8.76-8.70 (s, 1H); 8.32-8.20 (m, 2H); 8.22-8.06 (m, 4H); 7.65-7.59 (m, 1H); 7.58-7.10 (m, 23H).

Triplet energy of F1 was observed to be 2.52 eV.

Synthesis Example 2 (Synthesis of Compound F2)

In a 500 ml flask, a mixture of 4-(3-chlorophenyl)dibenzo[b,d]thiophene (17.2 g), 11,12-dihydroindolo[2,3-a]carbazole (15 g), Bis(dibenzylideneacetone)palladium(0) (1 g), sodium-tert-butoxide (16.68 g), tri-tert-butylphosphine (1.01 g) was added, and refluxed in xylene (375 ml) under nitrogen atmosphere. The reaction was monitored by thin layer chromatography. After the completion of the reaction, the reaction mixture was quenched with water (200 ml), and extracted using ethyl acetate (300 ml). The organic layer was extracted with water (5×50 ml), and dried over anhydrous sodium sulfate. The collected ethyl acetate layer passed through celite column chromatography for further purification. Subsequently, the ethyl acetate layer was evaporated to dryness in a rotary evaporator under vacuum. The residue was further precipitated by adding 200 ml n-hexane, filtered and dried under vacuum to yield 11-(3-(dibenzo[b,d]thiophen-4-yl)phenyl)-11,12-dihydroindolo[2,3-a]-carbazole (15.5 g).

In a 1 L flask, a mixture of 11-(3-(dibenzo[b,d]thiophen-4-yl)phenyl)-11,12-dihydroindolo[2,3-a]carbazole (15 g), sodium hydride (20.16 g), tetrahydrofuran (400 ml), were added together and stirred at 40° C. under nitrogen atmosphere. After an hour, 2-chloro-4,6-diphenyl-1,3,5-triazine (9.36 g) was added, and continued stirring overnight. The reaction was monitored by thin layer chromatography. After the completion of the reaction, the reaction mixture was quenched with water (120 ml) and extracted using ethyl acetate (200 ml). The organic layer was extracted with water (3×150 ml), and dried over anhydrous sodium sulfate. The collected ethyl acetate layer passed through celite column chromatography for further purification. Subsequently, the ethyl acetate layer was evaporated to dryness in a rotary evaporator under vacuum. The residue was further precipitated by adding 200 ml methanol, filtered and dried under vacuum. Compound F2 was obtained as a yellow colored solid in 16.5 g (76%) with a hplc purity 99%.

Compound F2 showed a melting point of 295.2° o and a glass transition temperature of 154° a.

1H NMR (CDCl3, 400 MHz) δ: 8.74-8.71 (d, 1H); 8.63-8.45 (s, 1H); 8.39-8.28 (t, 3H); 8.23-8.08 (m, 4H); 7.69-6.95 (m, 22H).

Triplet energy of F2 was observed to be 2.57 eV.

Synthesis Example 3 (Synthesis of Compound F3)

Following the procedure in the synthesis example F1, compound F3 was prepared in 36 g (66% yield) with a hplc purity of 99%.

Compound F3 showed a melting point of 251° o and a glass transition temperature of 144° a.

1H NMR (CDCl3, 400 MHz) δ: 8.59-8.62 (dd, 1H); 8.36-8.40 (m, 4H); 8.29-8.34 (m, 2H); 8.16-8.19 (dd, 1H); 8.11-8.14 (d, 1H); 7.91-7.94 (d, 1H); 7.73-7.75 (m, 1H); 7.56-7.65 (d, 4H); 7.39-7.52 (m, 7H); 7.34-7.37 (m, 1H); 7.26-7.3 (m, 3H); 7.20-7.24 (m, 3H); 6.99-7.06 (m, 2H).

Triplet energy of F3 was observed to be 2.67 eV.

Synthesis Example 4 (Synthesis of Compound F4)

Following the procedure in the synthesis example F2, compound F4 was prepared in 89 g (72% yield) with a hplc purity of 99%.

Compound F4 showed a melting point of 286° o and a glass transition temperature of 162° a.

1H NMR (CDCl3, 400 MHz) δ: 8.68-8.69 (d, 1H); 8.49-8.54 (d, 4H); 8.3-8.36 (m, 2H); 8.17-8.21 (d, 1H); 8.12-8.14 (d, 1H); 8.07-8.11 (d, 1H); 7.95-7.97 (m, 1H); 7.68-7.72 (m, 1H), 7.62-7.65 (m, 1H); 7.52-7.57 (t, 3H); 7.39-7.5 (m, 11H); 7.20-7.24 (dd, 2H); 7.07-7.11 (t, 1H); 6.81-6.83 (dd, 1H).

Triplet energy of F4 was observed to be 2.58 eV.

Synthesis Example 5 (Synthesis of Compound F5)

In a 1 L flask, a mixture of 11-(3-(dibenzo[b,d]furan-4-yl)phenyl)-11,12-dihydroindolo[2,3-a]-carbazole (20 g), sodium hydride (4.8 g), toluene (300 ml), was added, and stirred at 40° C. under nitrogen atmosphere. After an hour, 2-chloro-4,6-diphenyl-1,3-pyrimidine (12.8 g) was added and continued stirring at 80° f. The reaction was monitored by thin layer chromatography. After the completion of the reaction, the reaction mixture was quenched with water (200 ml) and extracted using ethyl acetate (150 ml). The organic layer was extracted with water (3×100 ml) and dried over anhydrous sodium sulfate. The collected ethyl acetate layer passed through celite column chromatography for further purification. Subsequently, the ethyl acetate layer was evaporated to dryness in a rotary evaporator under vacuum. The residue was further precipitated by adding 100 ml n-hexane, filtered and dried under vacuum. Compound F5 was obtained as a yellow colored solid in 18 g (85%) with a hplc purity more than 99%.

Compound F13 showed a melting point of 267° o and a glass transition temperature of 151° a.

1H NMR (CDCl3, 400 MHz) δ: 8.37-8.40 (m, 1H); 8.28-8.31 (d, 1H); 8.27-8.28 (t, 1H); 8.18-8.21 (m, 1H); 8.16-8.18 (d, 1H); 7.96-7.99 (dd, 1H); 7.92-7.96 (dd, 1H); 7.68-7.67 (t, 1H); 7.64-7.68 (m, 1H); 7.45-7.49 (m, 1H); 7.34-7.42 (t, 6H); 7.15-7.34 (m, 14H); 7.06-7.10 (m, 2H).

Triplet energy of F5 was observed to be 2.51 eV

Synthesis Example 6 (Synthesis of Compound F6)

Following the procedure in the synthesis example F5, compound F6 was prepared in 18 g (62% yield) with a hplc purity of 99%.

Compound F6 showed a melting point of 267° o and a glass transition temperature of 151° a.

1H NMR (CDCl3, 400 MHz), δ: 8.37-8.4 (m, 1H); 8.27-8.31 (m, 2H); 8.19-8.21 (m, 1H); 8.16-8.17 (d, 1H); 7.93-7.96 (d, 1H); 7.87-7.91 (m, 3H); 7.75-7.78 (m, 1H); 7.65-7.70 (m, 2H); 7.55-7.59 (m, 2H); 7.47-7.52 (m, 2H); 7.35-7.44 (m, 4H); 7.08-7.30 (m, 12H).

Triplet energy of F6 was observed to be 2.50 eV.

Synthesis Example 4 (Synthesis of Compound F13)

In a 1 L flask, a mixture of 11-(3-(dibenzo[b,d]furan-4-yl)phenyl)-11,12-dihydroindolo[2,3-a]-carbazole (20 g), sodium hydride (4.8 g), toluene (300 ml), were added together and stirred at 40° C. under nitrogen atmosphere. After an hour, 2-bromoethane (8.8 g) was added and continued stirring at 80° f. The reaction was monitored by thin layer chromatography. After the completion of the reaction, the reaction mixture was quenched with water (200 ml) and extracted using ethyl acetate (150 ml). The organic layer was extracted with water (3×100 ml) and dried over anhydrous sodium sulfate. The collected ethyl acetate layer passed through celite column chromatography for further purification. Subsequently, the ethyl acetate layer was evaporated to dryness in a rotary evaporator under vacuum. The residue was further precipitated by adding 100 ml n-hexane, filtered and dried under vacuum. Compound F13 was obtained as a yellow colored solid in 18 g (85%) with a hplc purity more than 99%.

Compound F13 showed a glass transition temperature of 108° o.

1H NMR (CDCl3, 400 MHz) δ: 8.21-8.23 (m, 1H); 8.19-8.21 (t, 2H); 8.11-8.13 (d, 1H); 8.05-8.07 (d, 1H); 7.98-8.00 (t, 1H); 7.93-7.97 (m, 2H); 7.56-7.65 (d, 4H); 7.68-7.74 (m, 2H); 7.62-7.65 (m, 1H); 7.51-7.54 (m, 1H); 7.29-7.46 (m, 4H); 7.12-7.15 (m, 1H); 3.75-3.85 (q, 2H); 0.90-0.96 (q, 3H).

Triplet energy of F13 was observed to be 2.51 eV

Synthesis Example 5 (Synthesis of Compound F15)

Following the procedure in the synthesis example F13, compound F15 was prepared in 36 g (66% yield) with a hplc purity of 99%.

Compound F15 showed a glass transition temperature of 109° o.

1H NMR (CDCl3, 400 MHz) δ: 8.19-8.21 (d, 1H); 8.15-8.19 (m, 3H); 8.11-8.12 (s, 1H); 8.09-8.11 (s, 1H), 8.03-8.04 (d, 1H); 7.99-8.02 (m, 1H); 7.72-7.75 (m, 1H); 7.64-7.68 (m, 3H); 7.69-7.61 (d, 1H); 7.47-7.53 (m, 1H); 7.34-7.45 (m, 5H); 7.28-7.3 (d, 1H); 7.12-7.15 (m, 1H); 3.74-3.80 (q, 2H); 0.85-0.95 (q, 3H).

Triplet energy of F15 was observed to be 2.52 eV.

Example 1 (Fabrication of Organic Electroluminescent Devices)

Prior to use, the substrate was degreased with solvents and cleaned in a UV ozone before it was loaded into the evaporation system. The substrate was then transferred into a vacuum deposition chamber for deposition of all other layers on top of the substrate. The following layers were deposited in the following sequence, as shown in FIG. 2, by evaporation from a heated boat under a vacuum of approximately $10^{-6}$ Torr:

a) a hole injection layer, HATCN
  b) a hole transport layer, HT1
  c) an exciton-blocking layer, BL (proprietary material from eRay optoelectronics Tech Co. Ltd, Taiwan)
  d) a light emitting layer, including a red phosphorescent dopant RD1, with a main host chosen from the patent examples (F1-F20) and a cohost CH1 (proprietary material from eRay optoelectronics Tech. Co. Ltd, Taiwan)
  e) an electron transport layer, ET
  f) an electron injection layer, LiF; and
  g) a cathode: approximately 150 nm thick, including Al.

The structure of the organic electroluminescent device may be denoted as: ITO/HATCN (15 nm)/HT (140 nm)/BL (15 nm)/3% RD1: Compound F4: CH1 (30 nm)/ET (30 nm)/LiF (1 nm)/Al (150 nm)

Comparative Example 1

Red electrophosphorecent device was fabricated as in the example 1, with CBP as the emitting host with RD1 in the emitting layer. The device structure may be denoted as: ITO/HATCN (15 nm)/HT (140 nm)/BL (15 nm)/3% RD1: CBP (30 nm)/ET (30 nm)/LiF (1 nm)/Al (150 nm).

Figure 4:
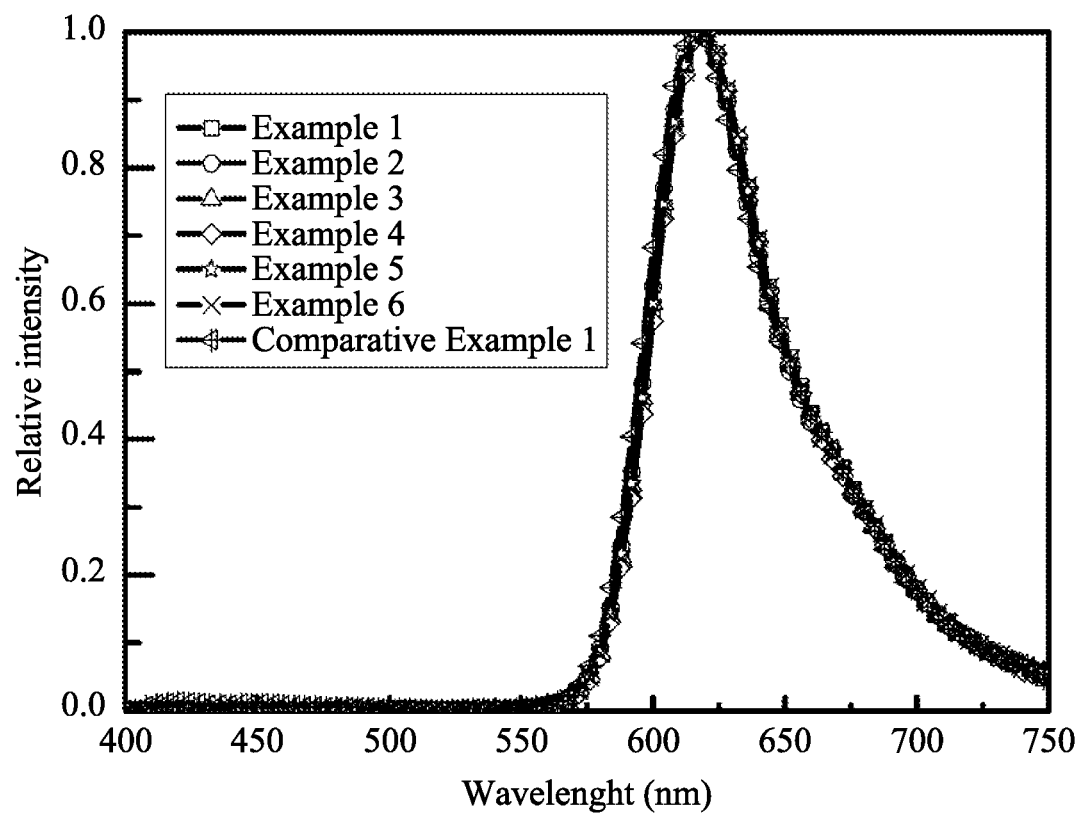
FIG. 4 shows the electroluminescent spectrum of the organic electroluminescent devices according to the present invention.

After the deposition of these layers, the device was transferred from the deposition chamber into a dry box for encapsulation, and subsequently encapsulated by using a UV-curable epoxy, and a glass lid containing a moisture getter. The organic electroluminescent device has an emission area of 3 $mm^2$. The organic electroluminescent device thus obtained was connected to an outside power source, and upon applying direct current voltage, emission of light with the characteristics shown in Table 2 were confirmed. The electroluminescent spectrum of this device is shown in FIG. 4.

The EL characteristics of all the fabricated devices in the present invention were evaluated using a constant current source (KEITHLEY 2400 Source Meter, made by Keithley Instruments, Inc., Cleveland, Ohio) and a photometer (PHOTO RESEARCH SpectraScan PR 650, made by Photo Research, Inc., Chatsworth, Calif.) at room temperature.

Operational lifetime (or stability) of the devices were tested at the room temperature and at an initial luminance of 10,000 $cd/m^2$ by driving a constant current through the devices. The color was reported using Commission Internationale de l'Eclairage (CIE) coordinates.

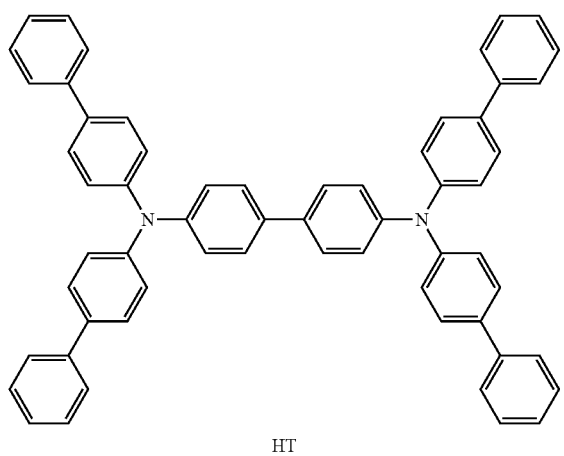

HT

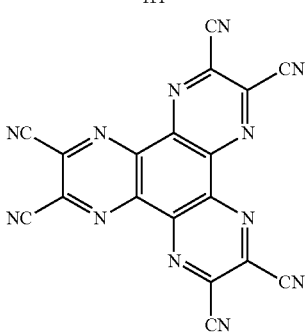

HAT-CN

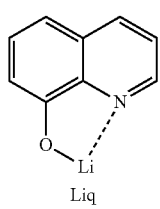

Liq

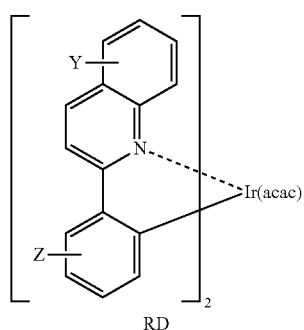

RD

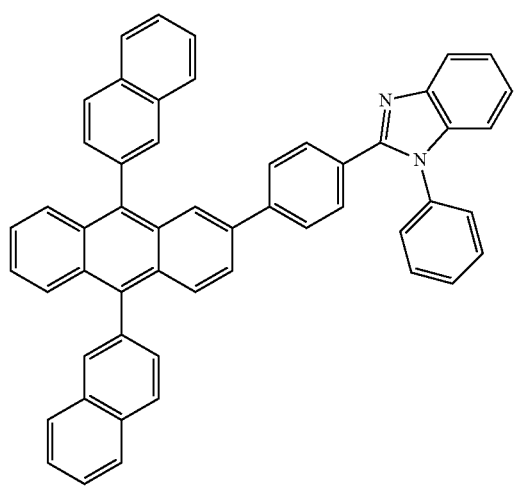

ET

-continued

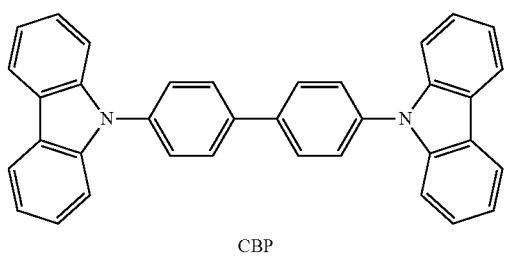 [SMILES: c1ccc2c(c1)c1ccccc1n2-c1ccc(-c2ccc(-n3c4ccccc4c4ccccc43)cc2)cc1 ; "CBP"]

CBP

Figure 5:
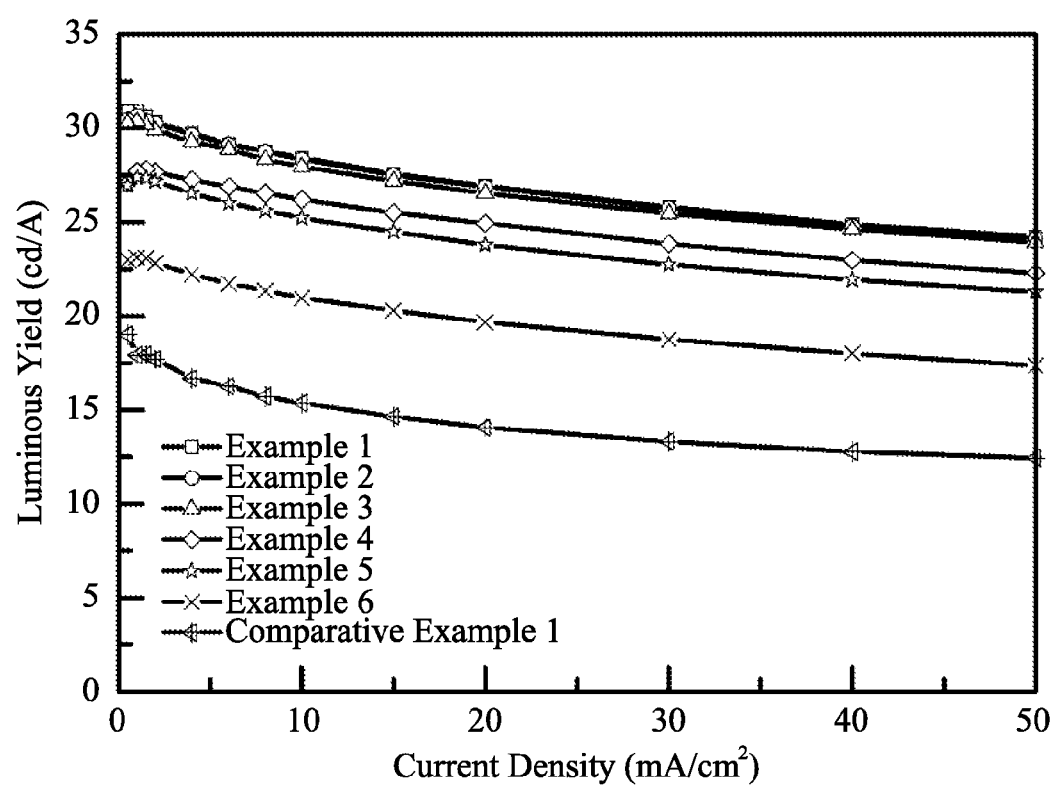
FIG. 5 shows the plot of luminous yield against current density of the electroluminescent devices according to the present invention.

The peak wavelength of emitted light, maximum luminous efficiency, and driving voltage and external quantum efficiency of the organic electroluminescent devices fabricated in the examples are shown in Table 2. A plot of current density vs luminance is shown in FIG. 5.

TABLE 2

| | Compound | Driving Voltage (V) | Max luminous efficiency (cd/A) | Emission wavelength (nm) | EQE (%) |
|---|---|---|---|---|---|
| Example 1 | F1 | 4.09 | 28.44 | 620 | 24.06 |
| Example 2 | F2 | 4.11 | 28.34 | 616 | 23.50 |
| Example 3 | F3 | 3.91 | 27.94 | 620 | 23.43 |
| Example 4 | F4 | 4.07 | 26.21 | 620 | 22.32 |
| Example 5 | F5 | 4.21 | 25.23 | 620 | 21.14 |
| Example 6 | F6 | 3.93 | 20.98 | 620 | 17.78 |
| Comparative Example 1 | CBP | 8.46 | 15.36 | 616 | 12.29 |

The present invention shall not be limited to the above described embodiments, methods and examples.

INDUSTRIAL APPLICABILITY

As described above in detail, the organic electroluminescent device having the material for the organic electroluminescent device of the present invention has high luminous efficiency, high thermal stability, sufficiently low driving voltage and long lifetime.

Therefore, the organic electroluminescent device of this invention is applicable to flat panel displays, mobile phone displays, light sources utilizing the characteristics of planar light emitters, sign-boards and has a high technical value.

The present invention has been described using exemplary preferred embodiments. However, it is to be understood that the scope of The present invention is not limited to the disclosed arrangements. The scope of the claims, therefore, should be accorded the broadest interpretation, so as to encompass all such modifications and similar arrangements.

The invention claimed is:
1. An organic material having the following Formula (I):

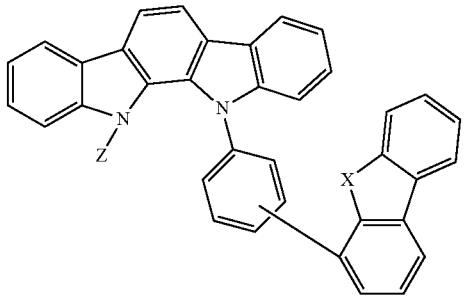

Formula 1 wherein X represents an oxygen or a sulfur atom; and Z represents a substituted or unsubstituted hetero-aromatic ring containing at least two nitrogens or an alkyl group with C2 to C6; and wherein the substituted or unsubstituted hetero-aromatic ring containing at least two nitrogens is selected from the group consisting of

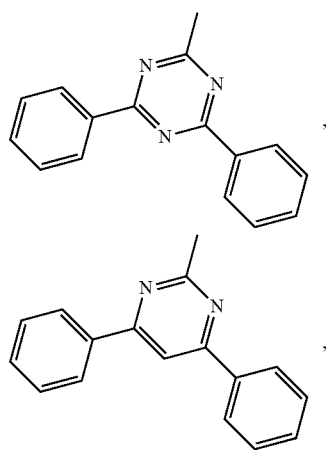

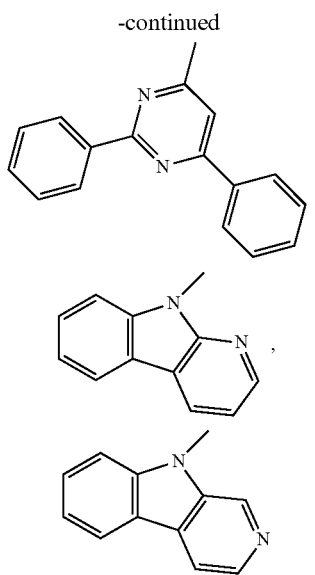

and

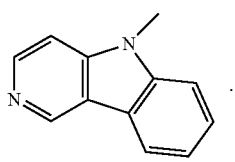

.

2. The organic material of claim 1, which has a triplet energy of more than 2.5 eV.

3. The organic material of claim 1, which is made into an amorphous thin film by means of vacuum deposition or wet process.

4. The organic material of claim 1, which is used in an organic layer.

5. The organic material of claim 4, wherein the organic layer has a thickness of between 1 nm and 500 nm.

* * * * *